United States Patent [19]

Schonwetter et al.

[11] Patent Number: 5,849,490

[45] Date of Patent: Dec. 15, 1998

[54] INDUCIBLE DEFENSIN PEPTIDE FROM MAMMALIAN EPITHELIA

[75] Inventors: Barry S. Schonwetter, Philadelphia; Michael A. Zasloff, Merion Station, both of Pa.

[73] Assignee: Magainin Pharmaceuticals, Inc., Plymouth Meeting, Pa.

[21] Appl. No.: 713,455

[22] Filed: Sep. 13, 1996

Related U.S. Application Data

[60] Continuation of Ser. No. 451,501, May 26, 1995, Pat. No. 5,656,738, which is a division of Ser. No. 248,016, May 24, 1994, Pat. No. 5,550,109.

[51] Int. Cl.$^6$ ..................................................... C12Q 1/68
[52] U.S. Cl. ................................................................ 435/6
[58] Field of Search ...................................................... 435/6

[56] References Cited

U.S. PATENT DOCUMENTS

| | | | |
|---|---|---|---|
| 5,202,420 | 4/1993 | Zasloff et al. | 530/324 |
| 5,242,902 | 9/1993 | Murphy et al. | 514/12 |
| 5,422,424 | 6/1995 | Selsted et al. | 530/324 |

OTHER PUBLICATIONS

Paul T. Brey, et al., "Role of the integument in insect immunity: Epicuticular abrasion and induction of cecropin synthesis in cuticular epithelial cells," Pro. Natl. Acad. Sci. USA, vol. 90 (Jul. 1993) pp. 6275–6279.

Gill Diamond et al., "Tracheal antimicrobial peptide, a cysteine–rich peptide from mammalian tracheal mucosa: Peptide islation and cloning of a cDNA," Proc. Natl. Acad. Sci. USA, vol. 88 (1991) pp. 1–6.

Michael E. Selsted et al., "Purification, Primary Structures, and Antibacterial Activities of Defensins, a New Family of Antimicrobial Peptides from Bovine Neutrophils," J. Biol. Chem. vol. 268, No. 9 (1993) pp. 6641–6648.

Thomas Ganz et al., "Defensins: macrobicidal and cytotoxic peptides of mammalian host defense cells," Medical Microbiology and Immunology, vol. 181 (1992) 99–105.

Diamond & Bevins, "Endotoxin up–regulates expression of an antimicrobial peptide gene in mammalian airway epithelial cells," Chest. 1994 Mar. 105 (3 Suppl) 51s–52s, 1994.

C. Kappler et al., "Insect Immunity. Two 17 bp Repeats Nesting a KB–Related Sequence Confer Inducibility to the Diptericin Gene and Bind a Polypeptide in Bacteria–Challenged Drosphila", EMBO J. 12(4): 1561–1568, Apr. 1993.

D.E. Jones et al., "Paneth Cells of the Human Small Intestine Express an Antimicrobial Peptide Gene", J. Biol. Chem. 267(32): 23216–23225, Nov. 1992.

Primary Examiner—Rebecca E. Prouty
Attorney, Agent, or Firm—Finnegan, Henderson, Farabow, Garrett & Dunner, L.L.P.

[57] ABSTRACT

The present invention relates to an inducible antimicrobial peptide designated lingual antimicrobial peptide (LAP) which has antibacterial and antifungal activity and which can be obtained from mammalian epithelium. The prepro- and the pro- precursors of LAP are also provided. The present invention also relates to cDNA encoding LAP, the prepro- precursor or the pro-lingual precursor. In addition, methods of treating microbial infection of the epithelia are provided. Such infections can be treated by contacting the epithelia with an antimicrobially effective amount of a purified mammalian epithelial LAP or by administering a component which cause endogenous production or up-regulation of LAP.

3 Claims, 6 Drawing Sheets

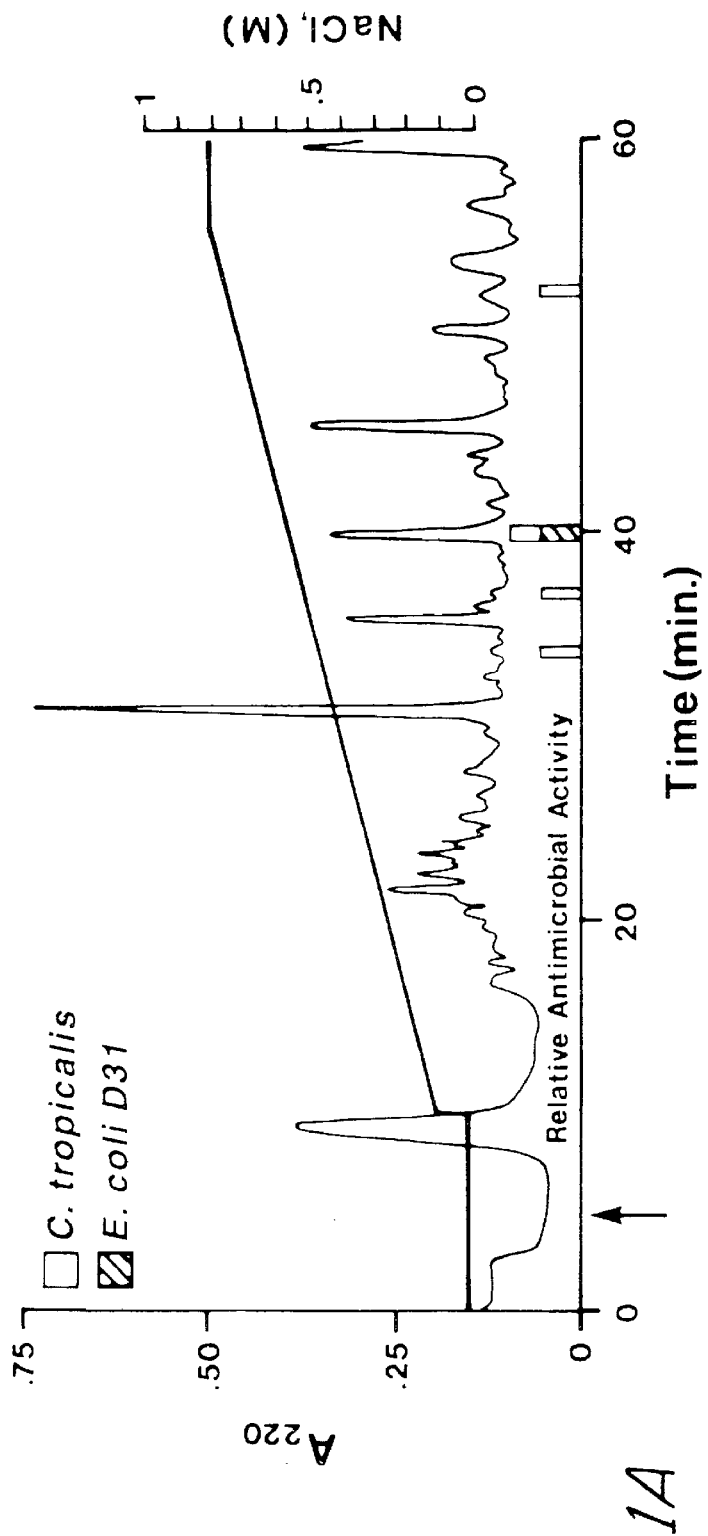

cDNA

```
          10         20         30         40         50         60         70
           |          |          |          |          |          |          |
CTCGTGCATTCGGCACCGACAGCATGAGGCTCCATCACCTGCTCCTTGCTCTTCCTGGTCCTGTCTG
                        M  R  L  H  H  L  L  L  A  L  L  F  L  V  L  S 80         90        100        110        120        130        140
           |          |          |          |          |          |          |
CTGGGTCAGGATTTACTCAAGGAGTAAGAAATTCTCAAAGCTGCCGTAGGAATAAAGGCATCTGTGTGCCGA
 A  G  S  G  F  T  Q  G  V  R  N  S  Q  S  C  R  R  N  K  G  I  C  V  P 150        160        170        180        190        200        210
           |          |          |          |          |          |          |
TCAGGTGCCCTGGAAGCATGAGACAGATTGGCACCTGTCTCTCGGAGCCCAAGTAAAATGCTGCAGGAGAAGT
 I  R  C  P  G  S  M  R  Q  I  G  T  C  L  G  A  Q  V  K  C  C  R  R  K 220        230        240        250        260        270        280
           |          |          |          |          |          |          |
AAAGAAGGCGAAACTGTGGCCAGACTGGATGCGGAGTCAGAAACTGTGCCCTTGGACAGAGAGTTAAAAT 290        300        310        320        330        340        350
           |          |          |          |          |          |          |
TTAAACCAGAATAAATTTGTTCAAAGTTAAAAAAAAAAAAAAAAAAAAAAAAAAAAAAAAAAAAAAAA
```

FIG. 2B

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

CCTCCTGCAG CATTTTACTT GGGCTCCGAG ACAGGTGCCA ATCTGTCT 48

( 2 ) INFORMATION FOR SEQ ID NO:2:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

AGCAGACAGG ACCAGGAAGA GGAGCGCAGA GGAGCAGGTG ATGGAGCCTC AT 52

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

ATGAGGCTCC ATCACCTG 18

( 2 ) INFORMATION FOR SEQ ID NO:4:

( i ) SEQUENCE CHARACTERISTICS:
        ( A ) LENGTH: 42 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Gln Gly Val Arg Asn Ser Gln Ser Cys Arg Arg Asn Lys Gly Ile Cys
 1               5                  10                  15
Val Pro Ile Arg Cys Pro Gly Ser Met Arg Gln Ile Gly Thr Cys Leu
                20                  25                  30
Gly Ala Gln Val Lys Cys Cys Arg Arg Lys
                35                  40
```

( 2 ) INFORMATION FOR SEQ ID NO:5:

( i ) SEQUENCE CHARACTERISTICS:
        ( A ) LENGTH: 64 amino acids
        ( B ) TYPE: amino acid (C) STRANDEDNESS: single
(D) TOPOLOGY: linear (ii) MOLECULE TYPE: peptide (xi) SEQUENCE DESCRIPTION: SEQ ID NO:5:

```
Met Arg Leu His His Leu Leu Leu Ala Leu Leu Phe Leu Val Leu Ser
 1               5                  10                  15
Ala Gly Ser Gly Phe Thr Gln Gly Val Arg Asn Ser Gln Ser Cys Arg
             20                  25                  30
Arg Asn Lys Gly Ile Cys Val Pro Ile Arg Cys Pro Gly Ser Met Arg
             35                  40                  45
Gln Ile Gly Thr Cys Leu Gly Ala Gln Val Lys Cys Cys Arg Arg Lys
             50                  55                  60
```

(2) INFORMATION FOR SEQ ID NO:6:

(i) SEQUENCE CHARACTERISTICS:
         (A) LENGTH: 127 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:6:

```
CAAGGAGTAA  GAAATTCTCA  AAGCTGCCGT  AGGAATAAAG  GCATCTGTGT  GCCGATCAGG       60
TGCCCTGGAA  GCATGAGACA  GATTGGCACC  TGTCTCGGAG  CCCAAGTAAA  ATGCTGCAGG      120
AGGAAGT                                                                    127
```

(2) INFORMATION FOR SEQ ID NO:7:

(i) SEQUENCE CHARACTERISTICS:
         (A) LENGTH: 133 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:7:

```
TTTACTCAAG  GAGTAAGAAA  TTCTCAAAGC  TGCCGTAGGA  ATAAAGGCAT  CTGTGTGCCG       60
ATCAGGTGCC  CTGGAAGCAT  GAGACAGATT  GGCACCTGTC  TCGGAGCCCA  AGTAAAATGC      120
TGCAGGAGGA  AGT                                                            133
```

(2) INFORMATION FOR SEQ ID NO:8:

(i) SEQUENCE CHARACTERISTICS:
         (A) LENGTH: 44 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:8:

```
Phe Thr Gln Gly Val Arg Asn Ser Gln Ser Cys Arg Arg Asn Lys Gly
 1               5                  10                  15
Ile Cys Val Pro Ile Arg Cys Pro Gly Ser Met Arg Gln Ile Gly Thr
             20                  25                  30
Cys Leu Gly Ala Gln Val Lys Cys Cys Arg Arg Lys
             35                  40
```

( 2 ) INFORMATION FOR SEQ ID NO:9:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

AGCAAGCATC TTACGTACTC TGACGTGC      28

INDUCIBLE DEFENSIN PEPTIDE FROM MAMMALIAN EPITHELIA

This is a continuation of prior application Ser. No. 08/451,501, filed May 26, 1995, now U.S. Pat. No. 5,656,738 which is a divisional of application Ser. No. 08/248,016 filed May 24, 1994, now U.S. Pat. No. 5,550,109.

BACKGROUND OF THE INVENTION

1. Field of the Invention

The present invention relates to inducible antimicrobial and antifungal peptides of the mammalian epithelial tissue. In particular, the present invention relates to a mammalian epithelial peptide designated lingual antimicrobial peptide (LAP) and to its precursor peptides. The invention present invention also relates to cDNA segments encoding LAP and its precursor peptides, and to methods of treating microbial infection of the epithelium.

2. Description of the Prior Art

Epithelium is a complex tissue responsible for forming an initial, physical barrier protecting the body against potentially harmful environments. Epithelial tissue covers the outer body surfaces and lines the luminal surface of the respiratory tract, the gastrointestinal tract, and the genitourinary system to protect these surfaces from exposure to the outside environment. Epithelial surfaces, therefore, serve a "defensive" function, protecting the host from the environment (Jacob and Zasloff, Ciba Foundation Symposium 186, 1994).

Antimicrobial peptides provide a second, chemical line of defense supplementing the physical barrier of the epithelial tissue surfaces. Antimicrobial peptides, produced by various tissues in the body, have antibacterial, antifungal, and antiviral activity. These peptides, which can be classified into several families, have been found in a variety of tissues from diverse species. For example, magainins have been isolated from frogs (Zasloff, M., Proc. Natl. Acad. Sci. USA 84: 5449–5453, 1987) and ceropins have been found in insects (Boman, H. G., Cell 65: 205–207, 1991). In addition, two groups of peptides within the defensin family have been identified. β-defensins have been isolated from neutrophils of cows (Selsted et al., J. of Biol. Chem. 268: 6641–6648, 1993) and from tracheal mucosa of cows (Diamond et al., Proc. Natl. Acad. Sci. USA 88: 3952–3956, 1991; and Diamond et al., Proc. Natl. Acad. Sci. USA 90: 4596–4600, 1993), while α-defensins have been isolated from neutrophils of humans (Lehrer et al., Annual Rev. Immunol. 11: 105–128, 1993) and from the epithelial-derived Paneth cells at the base of the crypts of the small intestine in murine and human GT tracts (Ouellette et al., J. Cell Biol. 108: 1687–1695, 1989; and Jones and Bevins, J. Biol. Chem. 267: 23215–23225, 1992). The antimicrobial peptides provide a second line of defense, killing bacteria and fungus pathogens which penetrate the physical barrier.

One example of epithelial tissue is the mammalian tongue which is covered by a dense stratified epithelium. The tongue is in an environment constantly exposed to various microorganisms that are part of the microbial flora of the mouth. Despite is constant exposure to microbials, invasive infections of the tongue rarely ensue even when abrasions occur on the tongue's surface. In investigating the infection resistance property of the mammalian tongue, a novel antibacterial and antifungal peptide was isolated from the extracts of bovine tongue epithelial tissue.

SUMMARY OF THE INVENTION

Accordingly, it is one object of the present invention to provide an inducible antimicrobial peptide having antibacterial and antifungal activity which can be obtained from mammalian epithelium, such as bovine tongue epithelium.

It is a further object of the present invention to provide the prepro-peptide and the pro-peptide precursors of the antimicrobial peptide.

It is another object of the present invention to provide cDNA that encodes the inducible mammalian epithelium antimicrobial peptide, the prepro-peptide and the pro-peptide.

It is yet a further object of the present invention to provide a method of treating microbial infections of the epithelium and microbial infections that extend through, beyond, or deeper in the epitheli, such as into connective tissue or the subdermal region.

Various other objects and advantages of the present invention will be apparent from the drawings and the following description of the invention.

In one embodiment, the present invention relates to a purified inducible mammalian epithelial lingual antimicrobial peptide (LAP) having an ion mass of about 4627.5 daltons, and having antimicrobial and antifungal activity.

In another embodiment, the present invention relates to a purified prepro-lingual antimicrobial peptide (prepro-LAP) or a purified pro-lingual antimicrobial peptide (pro-LAP).

In a further embodiment, the present invention relates to a cDNA encoding a lingual antimicrobial peptide, a prepro-lingual antimicrobial peptide, or a pro-lingual antimicrobial peptide.

In yet another embodiment, the present invention relates to a method of treating microbial infection of the epithelia. The method comprises contacting the epithelia with an antimicrobially effective amount of a purified mammalian epithelial lingual antimicrobial peptide (LAP) having an ion mass of about 4627.5 daltons, and having antimicrobial and antifungal activity so that the microbial infection is inhibited.

In yet a further embodiment, the present invention relates to a method of inducing endogenous expression of lingual antimicrobial peptide (LAP) to treat microbial infections. Endogenous expression is induced by administering to a patient in need thereof, an effective amount of a component which induces the production of LAP by epithelial tissue.

In another embodiment, the present invention relates to a method of identifying endogenous up-regulators of lingual antimicrobial peptide (LAP). The method comprises contacting an epithelial cell culture with a test substance and measuring the level of mRNA to determine whether the test substance is an up-regulator.

In a further embodiment, the present invention relates to another method of identifying endogenous up-regulators of lingual. antimicrobial peptide (LAP). Up-regulators of LAP can be identified by constructing an expression vector containing a β-defensin gene promoter operably linked to a reporter gene, infecting a host cell with the expression vector, and culturing the host cell in the presence of test substances. Whether the test substance is an up-regulator is then determined by measuring the level of mRNA or reporter gene expression.

BRIEF DESCRIPTION OF THE DRAWINGS

FIG. 1A shows strong cation exchange chromatography of bovine tongue epithelial extracts.

FIG. 2A shows the peptide sequence of LAP, TAP, and β-defensin consensus.

FIG. 2B shows the cDNA sequence of LAP.

DETAILED DESCRIPTION OF THE INVENTION

Figure 1B:
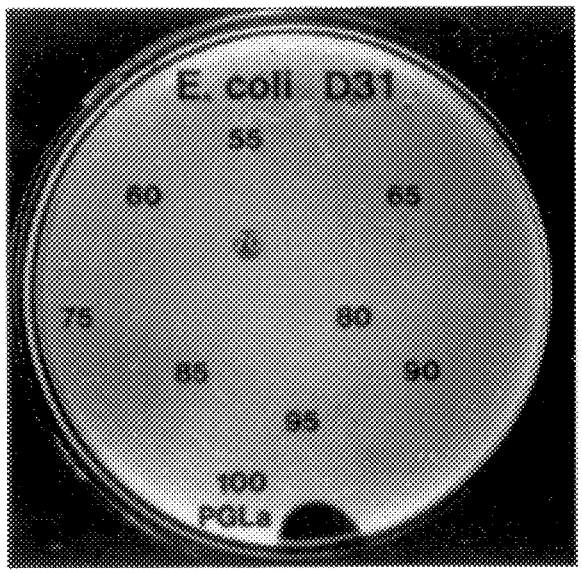
FIG. 1B shows a plate assay of high phase liquid column (HPLC) column fractions which was done to access antimicrobial activity on a lawn of *E. coli* D31.

The present invention relates to an inducible antimicrobial peptide designated lingual antimicrobial peptide (LAP). LAP is a mammalian antimicrobial peptide which has an ion mass of about 4627.5 daltons and possesses both antimicrobial and antifungal activity. In one embodiment of the present invention, LAP has amino acid sequence: QGVRNSQSCRRNKGICVPIRCPGSMRQIGTCLGAQVKCCRRK. This peptide, obtainable from bovine epithelial tissue, is a member of the defensin family of antimicrobial peptides. LAP belongs to the β-defensin group of peptides as LAP contains the 11 conserved amino acid residues shared by all β-defensins. In addition, the signal sequence of LAP is similar to the signal sequence of the tracheal mucosa antimicrobial peptide (TAP), a β-defensin described by Diamond et al. (Diamond et al., Proc. Natl. Acad. Sci. USA 88: 3952–3956, 1991).

Antimicrobial peptides of the defensin family have been found in several species including humans, rabbits, rats, mice, and guinea pigs (Ganz et al., Med. Microbiol. Immunol. 181: 99–105, 1992; and Lehrer et al., Annual Rev. Immunol. 11: 105–128, 1993). Defensins of bovine origin have been placed in the β-defensin group while homologous defensins of human origin are designated α-defensins. As defensin peptides exist in many mammalian species, the present invention relates to all mammalian LAP including, but not limited to, LAP of bovine origin and LAP of human origin. Homologous LAPs from species other than cows can be obtained, for example, using the isolation strategy employed with the bovine tongue extracts or using cDNA probes. For example, epithelial tissue from humans could be probed using the LAP 48-mer probe: 5'-CCT-CCT-GCA-GCA-TTT-TAC-TTG-GGC-TCC-GAG-ACA-GGT-GCC-AAT-CTG-TCT-3', or the signal sequence 51-mer probe: 5'-AGC-AGA-CAG-GAC-CAG-GAA-GAG-GAG-CGC-(AG)AG-GAG-CAG-GTG-ATG-GAG-CCT-CAT-3', or the human α-defensin signal sequence which is highly conserved (Jones and Bevins, J. Biol. Chem. 267: 23215–23225, 1992). This would identify tissue that would contain either α or β defensin. One could purify the defensin peptide from this tissue or clone the corresponding cDNA by reverse transcribing the poly-A RNA message obtained from these tissues. Alternatively, one could make a cDNA library from these tissues and then clone the corresponding cDNA from the library using the probes described above and standard molecular biology techniques (Sambrook, Molecular Cloning: A Laboratory Manual, Cold Spring Harbor Laboratory (New York, 1989)).

LAP has broad spectrum antimicrobial activity against Gram-negative bacteria, Gram-positive bacterial and fungal pathogens. The peptide may also have antiviral activity. For example, LAP has a specific activity against *Escherichia coli* of 16–32 µg/ml, *Pseudomonas aeruginosa* of 63–125 µg/ml, *Staphylococcus aureus* of 63–125 µg/ml, *Candida albicans* of 32–63 µg/ml, and *Candida tropicalis* of 16–32 µg/ml.

When translated from mRNA the peptide of the present invention, LAP, begins as a prepro-precusor peptide, designated prepro-LAP. This precursor peptide contains a signal sequence consisting of about 20 amino acids followed by a short putative pro sequence consisting of about 2 amino acids. Thus, the present invention relates to the prepro-LAP and the pro-LAP precursor peptides as well as to LAP. Indeed, in one embodiment of the present invention, prepro-LAP has amino acid sequence: MRLHHLLLALLFLVLSAGSGFTQGVRNSQSCRRNK-GICVPIRCPGSMRQIGTCLGAQVKCCRRK, and in a further embodiment, pro-LAP has amino acid sequence: FTQGVRNSQSCRRNKGICVPIRCPGSMR-QIGTCLGAQVKCCRRK.

While the present invention is exemplified with the purification of LAP from bovine tongue epithelia, the skilled artisan will understand that the peptides of the present invention can be purified, that is isolated from proteins with which they are normally associated, from other epithelial tissues. Suitable epithelial tissues include, but are not limited to, epithelia from the respiratory tract, such as trachea, bronchi, and lung tissue, the gastrointestinal tract, such as cecum, colon, and rectum tissue, the genitourinary tract, such as bladder tissue, the reproductive tract including testes, and facial epithelia, such as conjunctiva. Further, in addition to using peptide purification methods, peptides of the present invention can be chemically synthesized or recombinantly produced using standard techniques in the art.

The present invention also relates to cDNA which encode the prepro-LAP, pro-LAP and/or LAP peptides. In particular, cDNA of the present invention include nucleotide sequences which code for an amino acid sequence selected from the group consisting of: QGVRN-SQSCRRNKGICVPIRCPGSMRQIGTCLGAQVKCCRRK, MRLHHLLLALLFLVLSAGSGFTQGVRNSQSCRRNK-GICVPIRCPGSMRQIGTCLGAQVKCCRRK, and FTQGVRNSQSCRRNKGICVPIRCPGSMR-QIGTCLGAQVKCCRRK. Examples of cDNA of the present invention include, but are not limited, the nucleotide sequences of FIG. 2B.

The present invention further relates to recombinant DNA molecules comprising a vector and a cDNA encoding prepro-LAP, pro-LAP or LAP. Possible vectors include, but are not limited to, Bluescript, Bluescript II, pGEM, pRIT, and PET vectors. Host cells transformed with these recombinant DNA molecules using standard techniques can be cultured to provide a source of LAP or its precursor peptides. Suitable host cells include eukaryotic and prokaryotic cells such as yeast, *E. coli,* DH5α, and HB101.

While LAP is constitutively expressed at low levels in mammalian epithelia, high levels of mRNA expression are induced in response to epithelia injury and/or infection. For example, increased concentrations of LAP mRNA are found in epithelia surrounding acute and chronic areas of infection or inflammation. This suggests that LAP plays a role in innate immunity. According to Janeway (Janeway, C. A. J. Jr., Immunology Today 13: 11–16, 1992), innate immunity is characterized by three properties: polyspecificity, ability to discern self from nonself, and rapid response kinetics.

LAP of the present invention is a broad spectrum antibiotic which is polyspecific and inducible upon infection, with induction occurring rapidly enough to be present in areas of acute inflammation. These findings are consistent with each of Janeway's hypotheses and suggests that LAP plays a role in innate immunity protecting epithelia from injury and infection.

Accordingly, peptides of the present invention can be used to treat epithelial diseases and microbial infections. LAPs can be used to treat epithelial diseases such as, diseases occurring in any immunodeficiency state, cystic fibrosis, and gum diseases and. wounds, as well as microbial infections of the epithelia such as, bacterial and viral infection, and infections that extend through, beyond, or deeper in the epithelial such as into the connective tissue or subdermal regions. To treat such conditions, the diseased or infected epithelial tissue is contacted an antimicrobially effective amount of LAP or a precursor of LAP, either alone or in a pharmaceutically acceptable carrier. Suitable carriers include cremes, gels, saline, water, paste, and liposomes made of phospholipids. The LAP administered in this manner can be purified from epithelial tissue, recombinantly produced using the recombinant vector of the present invention or chemically synthesized.

The effective amount of LAP will vary depending on several factors such as, for example, the severity of the disease or infection, the causative organism and the type of epithelial tissue being treated, but the amount required for a particular patient given the patient's history and symptoms is easily determinable by one skilled in the art. For example, LAP could be applied to gums with gingivitis in micromolar amounts greater than the minimum inhibitory concentration (MIC) of LAP for Staphylococcus. LAP could be used as an antifungal in the mouth or GI tract since it has activity against *Candida albicans* and *Candida tropicalis*, in vitro and can be administered in a dose that provides a local tissue level greater than the MIC for that organism or in several smaller doses that can be repeated.

In addition, in the respiratory tract one could use LAP to treat pneumonia, bronchitis, or cystic fibrosis. For example, LAP could be inhaled, aerosolized, placed in a liposome and inhaled, or lavaged into the respiratory tract. These formulations could also be used to place the LAP in contact with the genitourinary or reproductive tracts. LAP could also be applied directly to a skin wound, burn or infection.

Lingual antimicrobial peptides or other α and β defensins can also play a role in preventing or treating diseases by inducing endogenous defenses. Components of infection, such as bacterial cell wall lipopolysaccharides, inactivated microbes, glycolipids, glycoproteins, sugars, or viral components, can be identified which induce the expression of LAP mRNA in epithelial tissues. Such components can be identified using standard techniques such as those employed by Brey et al. (Proc. Natl. Acad. Sci. USA 90: 6275–6279, 1993), and Diamond and Bevins (Chest. 1994 March 105(3 Suppl) 51s–52s, 1994). Accordingly, the present invention also provides methods of screening test substances to determine whether they are up-regulators of LAP. For example, cultures of epithelial cells capable of expressing LAP can be exposed to various components and the amount of mRNA produced by the cells measured to determine whether exposure to a given component increased the mRNA expression. Alternatively, an expression vector system could be designed with a β-defensin promoter operably linked to a reporter gene. Suitable reporter genes included chlorampherical acetyl transferase or β-galactosidase. Host cells infected with such an expression vector could be cultured in the presence of test substances and the ability of these substances to up-regulate LAP or other α and β defensins determined by measuring the level of mRNA produced by the host cell or by measuring the increase in message as a function of reporter gene expression.

Components which are shown to induce the expression of LAP mRNA can then be administered to a patient to induce therapeutic endogenous expression of LAP. The induction of endogenous LAP production can be used to treat, for example, patients with AIDS, severe microbial infections, inflammatory skin or gum lesions, or infections of any epithelial surface or infections that extend through, beyond, or deeper in the epithelial, such as into the connective tissue or subdermal regions.

For the purposes of illustrating a preferred embodiment of the present invention, in the following non-limiting examples, the lingual antimicrobial peptide (LAP) was isolated from bovine tongue epithelial tissue, the cDNA encoding LAP was isolated and sequence, and mRNA expression and tissue distribution analyzed. It is, however, to be understood that the discussion generally applies to the isolation of LAP or other defensins from any mammalian epithelium.

EXAMPLES

Purification of LAP Peptide

Using a purification scheme that involved organic extraction, gel filtration, reverse phase HPLC, and strong cation exchange HPLC, the lingual antimicrobial peptide (LAP) was purified from bovine tongue epithelial tissue.

Approximately 500 g of anterior tongue epithelial tissue was dissected from 5 freshly killed cows and frozen in liquid nitrogen. The tissue was pulverized in a blender using liquid nitrogen and extracted for 3 days at 40° C. with 5 volumes of 60% acetonitrile, 1% Trifluoroacetic Acid (TFA). The sample was then centrifuged at 4° C. for 15 minutes and the supernatant was extracted using 15 volumes chloroform-:methanol (2:1). The upper aqueous phase was pooled, lyophilized, and resuspended in 15 ml of 25% acetonitrile, 1% TFA. The sample was then centrifuged at 4000 RPM for 15 minutes and the remaining supernatant was loaded on a, 120 ml P-30 gel filtration column (Biorad, Richmond, Calif.).

The active antimicrobial fractions were pooled and loaded onto a reverse phase HPLC C-18 column (Poly LC, Columbia, Md. The active fractions were the loaded onto a strong cation exchange HPLC column-PSEA (Poly LC, Columbia, Md.) (FIG. 1A) and each fraction was desalted using a C-18 Sep-pak cartridge (Waters, Milford, Mass.), dried overnight and assayed for activity against *E. coli* D31 and *C. tropicalis* as described below.

This peptide was the most abundant of several antimicrobial activities isolated from the bovine tongue epithelium. The minimal inhibitory concentrations (MIC's) demonstrated broad spectrum antimicrobial activity against gram negative and gram positive bacteria, and fungal pathogens with a potency similar to magainin-II amide (FIG. 1C) and comparable to other defensins previously isolated. (Diamond et al., Proc. Natl. Acad. Sci. USA 88: 3952–3956, 1991.)

Antimicrobial Assaying of LAP Peptide

Figure 1C:
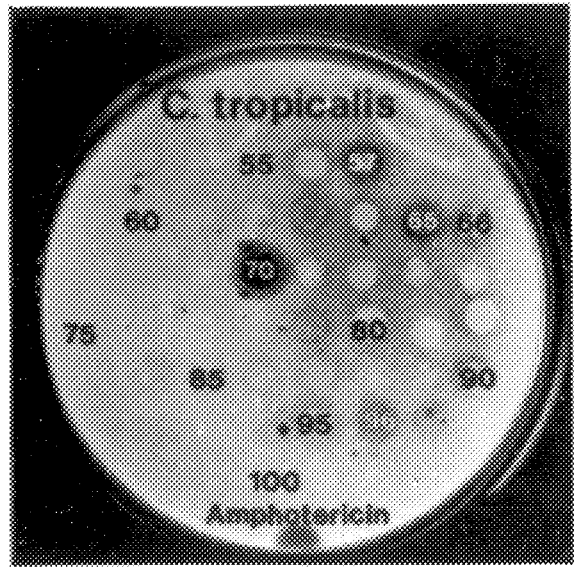
FIG. 1C shows a plate assay which accesses antimicrobial activity against *C. tropicalis.*

Antimicrobial activity was determined during the purification process. Approximately 2.5 ml fractions from the P-30 gel filtration column were assessed after drawing fractions and taking an aliquot of the fraction and spotting that fraction on a radial diffusion plate as described by Zasloff, M. (Proc. Natl. Acad. Sci USA 84: 5449–5453, 1987) against *E. coli* D31 or fungal pathogens such as *Candida albicans, Candida tropicalis,* or *Staphylococcus aureus*. (See also, Zasloff et al., Proc. Natl. Acad. Sci. USA 85: 910–913, 1988.) (FIG. 1B and 1C.) Briefly, the minimal inhibitory concentrations (MIC's) were assessed using a 96 well microtitre plate (Corning Glass Works, Corning, N.Y.). Microorganisms were grown in log phase at ¼ strength tryptics soy broth (TSB) at a density of $1\times10^5$/ml. The assays used ¼ strength TSB. For each organism, dilutions of peptide were made ranging from >500 µg/ml to 1 µg/ml using ¼ strength TSB as a dilution buffer. Zones of bacterial growth or lack of growth were assessed under the microscope. MIC's were calculated based the lowest concentration of peptide that inhibited growth.

The results set forth below in Table 1 demonstrate that LAP has broad spectrum antimicrobial activity against Gram-negative bacteria, Gram-positive bacteria, and fungal pathogens. Indeed, the MIC's demonstrated broad spectrum antimicrobial activity against gram negative and gram positive bacteria, and fungal pathogens with a potency similar to magainin-II amide and comparable to other defensins previously isolated (Diamond et al., Proc. Natl. Acad. Sci. USA 88: 3952–3956, 1991).

TABLE 1

Antimicrobial Activity of LAP and Magainin II-amide

| Microorganism (ATCC) | Minimum Inhibitory Concentration (µg/ml) | |
|---|---|---|
| | LAP | Magainin II |
| *Escherichia coli* (D31) | 16–32 | 13–25 |
| *Pseudomonas aeruginosa* (27853) | 63–125 | 13–25 |
| *Staphylococcus aureus* (29213) | 63–125 | 50–100 |
| *Candida albicans* (14053) | 32–63 | 50–100 |
| *Candida tropicalis* (13803) | 16–32 | 13–25 |

Sequencing LAP Peptide

The mass ion of LAP is 4627.5, consistent with the size and amino acid composition of a β-defensin (FIG. 2A) (Selsted et al., J. of Biol. Chem. 268: 6641–6648, 1993.) The carboxyl (C) terminal sequence of approximately 20 amino acids of LAP were determined using microsequencing after digestion of the purified peptide with trypsin, followed by reduction and alkylation of cysteine residues (FIG. 2). Briefly, the peptide fragments were sequenced using Edman degradation, a standard sequencing technique. The order of the sequenced fragments was determined with overlapping fragments or identifying homologous regions to TAP.

A polymerase chain reaction (PCR) based strategy was designed to complete the N-terminal sequence. After microsequencing, degenerate PCR primers were designed from the carboxyterminal region of the LAP amino acid sequence where there was no sequence homology to TAP and codon assignment of TAP was used for homologous amino acids. A non-degenerate primer was designed from the first six amino acids of the signal sequence derived from the cloning of the cDNA of TAP.

The primers were sense strand 5'-ATGAGGCTCCATCACCTG (non-degenerate) and 5'-(AG)CA(AG)CA(TC)TT(ACGT)AC(TC)TG(ACGT)GC-antisense strand (1:256 degeneracy). PCR conditions were 95° C. for 1 minute, 58° C. for 2 minutes, and 72° C. for 3 minutes. This was followed by 72° C. for 15 minutes. PCR products were run on an 1.2% agarose gel, purified with Geneclean II, and subcloned into Bluescript vector modified to accept PCR products after linearization with EcoRV. The cDNA product was sequenced using dideoxy chain termination end was identical with the amino acid sequence of LAP derived from microsequencing.

Cloning and Sequencing of LAP Peptide cDNA

A cDNA library was generated from bovine tongue epithelial poly A(+) RNA (Stratagene Kit for λZAP library, La Jolla, Calif.) and the cDNA for LAP was cloned and sequenced (FIG. 2B). Briefly, a cDNA lambda Zap-cDNA library of tongue epithelial tissue was constructed from (2 µg) poly A(+) RNA and inserts were size selected from 0.1 kb to 3 kb. Approximately $0.5 \times 10^6$ phage were spread over 10 plates and there were approximately 100 positive pfu's per plate. The phage were isolated using a LAP cDNA probe derived from PCR containing the signal sequence and the peptide coding region (183 bp). Duplicate lifts to detect positives were used with Genescreen II nylon membranes (Dupont NEN, Boston, Mass.). The phage were plaque purified and approximately 6 positive phage were isolated, subcloned into Bluescript and sequenced using T3 and T7 primers and dideoxy chain termination. The sequence was confirmed in triplicate using sequences derived from multiple clones.

The cloned message encodes a 64 amino acid precursor, structurally similar to the prepro β-defensin, TAP (Diamond et al., Proc. Natl. Acad. Sci. USA 88: 3952–3956, 1991). The signal sequence consists of 20 amino acids followed by a short putative pro sequence consisting of 2 amino acids which could be cleaved by a dipeptidase as described for the antimicrobial mellitin (Boman et al., J. Biol. Chem. 264: 5852–5860, 1989; and Kreil, G., TIBS 15: 23–26, 1990). The mature peptide is at the C terminus of the precursor and consists of 42 amino acids followed by an in frame stop codon. The polyadenylation signal is 14 nucleotides from the poly A tail.

Expression and Distribution of LAP mRNA in Epithelia Tongue Tissue

Figure 3A:
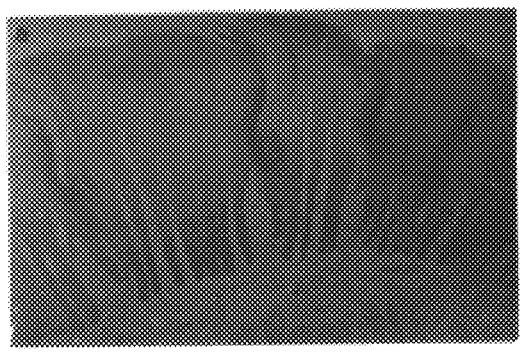
FIGS. 3A–F show the induction of LAP message surrounding areas of infection. Figures A and B show normal expression of LAP mRNA in bovine tongue epithelium using in-situ hybridization while Figures C–F show representative in-situ hybridization of naturally occurring bovine tongue lesions. Figures G–H are higher powered view of Figures E–F, respectively.

The bovine tongue is covered by a dense parakeratinized stratified epithelium (FIG. 3A). The upper surface of the epithelium is comprised of senescent cells while the middle and basal layers represent transcriptionally active cells (Fuchs, E., J. Cell Biol. 111: 2807–2814, 1990). The basal layer of the epithelium is comprised of germinal cells. The epithelium is nourished by a connective tissue layer which forms papillae within the epithelium, and contains blood vessels and nerves. There is a striated muscular layer inferior to the connective tissue. To determine the expression and distribution pattern of LAP mRNA, bovine tongue tissue was hybridized with the LAP antisense probe.

Bovine tongue was obtained from Moyer Packing Company (MOPAC) (Souderton, Pa.) using freshly slaughtered cows (Jersey Holstein and black angus species). The anterior epithelium was dissected from the underlying connective and muscle tissue and the epithelial tissue was fixed immediately using 4% paraformaldehyde, 1×PBS. The tissue was embedded in a paraffin block and 6–8 µicron thick sections were cut and mounted on sialanated slides. The slides were maintained at −70° C.

Riboprobes were made with a full length cDNA of LAP subcloned into Bluescript, and linearlized with Sma and Kpn I enzymes for sense and antisense transcripts, respectively.

The slides were dried and fixed using standard in-situ conditions (Young et al., Neurosci. Lett. 70: 198–203, 1986) and hybridizations were carried out at 37° C. with overnight incubations using 2×10⁶ cpm/slide. The slides were washed at high stringency of 65° C., with β-mercaptoethanol and the slides were exposed to autoradiographic film. The slides were dipped in photographic emulsion, Kodak NTB-2 prior to exposure of the emulsion to the slides for 4½ weeks at 40° C. The slides were developed under standard conditions, then stained with hematoxalin and eosin, and photographed at 20–40× magnification.

Figure 3B:
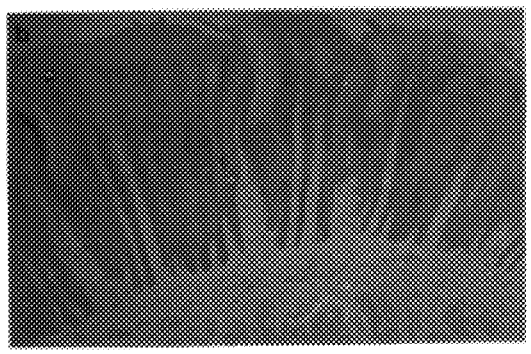
Figure 3C:
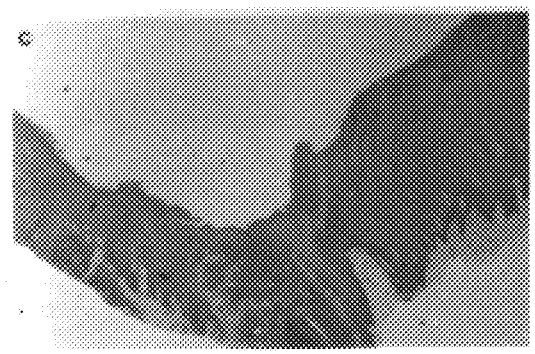
Figure 3D:
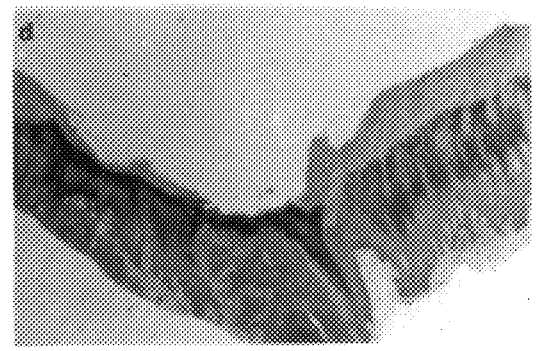
Figure 3E:
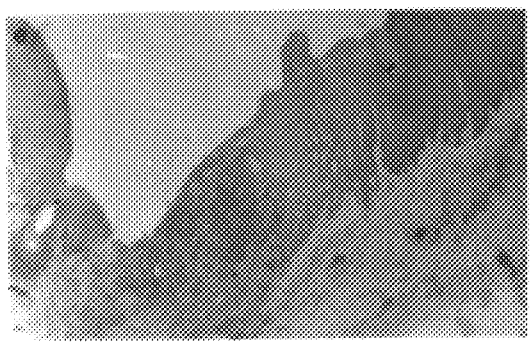
Figure 3F:
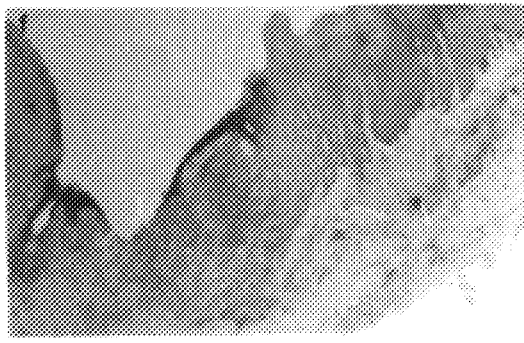

Intense hybridization to the middle layers of the epithelium was seen in FIG. 3B. (FIG. 3A represents the sense-negative control.) The sense probe yielded no hybridization signal. In contrast, the mRNA for β tubulin appeared to be distributed uniformly throughout the entire tissue section.

Although tongue epithelium has been identified as the major site of LAP tissue expression, the cellular pathways of processing or secretion have not yet been determined. Since the LAP precursor contains a signal sequence, it should be secreted from individual epithelium cells or into intracellular granules. LAP could be secreted in the pro form and processed post translationally as suggested for human defensins (Ganz et al., Blood 82: 641–650, 1993).

To discern the role of LAP in innate immunity, three cows with naturally occurring tongue lesions were selected. In all three cases, the lesions represented areas consisting of both acute and chronic infection and inflammation (FIG. 3C–3F). In each case, destruction of the normal epithelium was noted. There were areas of acute inflammation characterized by hemorrhage and erythrocyte accumulation, infiltration of polymorphonuclear leukocytes, along with areas of more chronic inflammation characterized by infiltration of mononuclear cells. The area surrounding and including the tongue lesions were excised from the three cows and fixed in 4% paraformaldehyde/PBS prior to in-situ hybridization. In-situ hybridization was performed as described above. The lesions were hybridized with either full length riboprobes for LAP (sense and antisense) or β-tubulin (sense and antisense). All slides were exposed to emulsion for 4½ weeks prior to developing.

An increase in the concentration of LAP mRNA was found in the remaining epithelia surrounding both acute and chronic areas of infection. The pattern of expression is consistent with induction of LAP mRNA in the existing cells of the epithelium surrounding the infection.

These observations parallel the experimental data of Brey et. al. who showed induction of cecropin mRNA in the epithelial cell layer of silkworm larvae after epicuticular and cuticular wounding (Brey et al., Proc. Natl. Acad. Sci. USA 90: 6275–6279, 1993). Induction only occurs when the abraded larvae are challenged with live bacteria or bacterial cell wall components. Diamond et al. showed in an in vitro system that TAP mRNA from primary cultured bovine tracheal epithelial cells was induced 5-fold by adding LPS to the culture medium (Diamond and Bevins, Chest 105(3 Suppl) 51s–52s, 1994). The sequences of the gene from the bovine defensin TAP, and both the cecropin and a dipthericin loci from drosophila, contain an nFκB site in the 5' region implicated in the LPS responsiveness of these genes (Diamond et al., Proc. Natl. Acad. Sci. USA 90: 4596–4600, 1993; Kapper et al., EMBO J. 12: 1561–1569, 1993; and Sun and Faye, Europ. J. Biochem. 204: 885–892, 1992).

For tissue distribution studies, epithelia from the gastrointestinal, respiratory, genitourinary, male and female reproductive tracts of cows and facial cow epithelia was employed. Northern blot were performed on bovine tissues. RNA was prepared from bovine epithelial tissue specimens taken from freshly killed cows. Tongue RNA was also obtained from mixed gestation aged fetal tongue (Moyer Packing Company, Souderton, Pennsylvania) and from 4 month old milk fed veal calves (March Farms, Souderton, Pa.). The tissue was immediately frozen in liquid nitrogen. RNA was prepared after quanidinium isothiocyanate extraction followed by centrifugation of the RNA on a cesium chloride cushion. For the poly A(+) blot, RNA was isolated from 200 μg of total RNA, followed by isolation of poly (A)+ RNA using oligo dT push columns. 4 μg of poly (A)+ RNA from several tissues were electrophoresed on a 1.2% formaldehyde gel using 1×MOPS as a running buffer. Approximately 15 μg of total RNA was used from each specimen. The tissues were also run on a 1.2% formaldehyde gel. The gels were blotted using Zetabind positively charged nylon membranes, transferring the RNA using 10×SSC at pH 7.4. Hybridizations were carried out at 42° C., using standard hybridization conditions of 6×SSC, 5×Denhardt's, 20% formamide, 200 μg/ml of yeast RNA, 0.5% SDS. Probes were designed as follows:

LAP (48 mer): 5'-CCT-CCT-GCA-GCA-TTT-TAC-TTG-GGC-TCC-GAG-ACA-GGT-GCC-AAT-CTG-TCT-3'.

Signal sequence (51 mer): 5' -AGC-AGA-CAG-GACCAG-GAA-GAG-GAG-CGC-(AG)AG-GAG-CAG-GTG-ATG-GAG-CCT-CAT-3'.

The probes were each end labelled using $Y^{32}$p-ATP to a specific activity of $1\times10^8$ CPM/μg DNA. The β-tubulin probe was the full length cDNA bovine clone and was labelled with $\alpha^{32}$P dCTP using random priming to a specific activity of $1\times10^9$ CPM/μg DNA. The blots were hybridized overnight and washed at the following conditions:

LAP—65° C., 1×SSC, 0.1% SDS; and βtubulin—65° C., 0.1×SSC, 0.1% SDS.

Figure 4A:
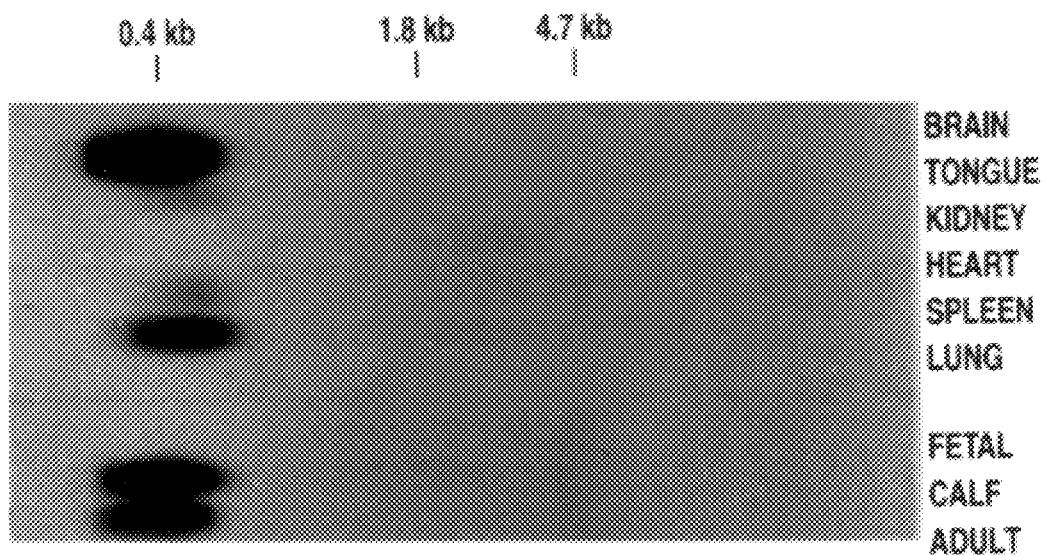
FIGS. 4A and 4B show the developmental expression and tissue distribution of bovine mRNA for LAP.
Figure 4B:
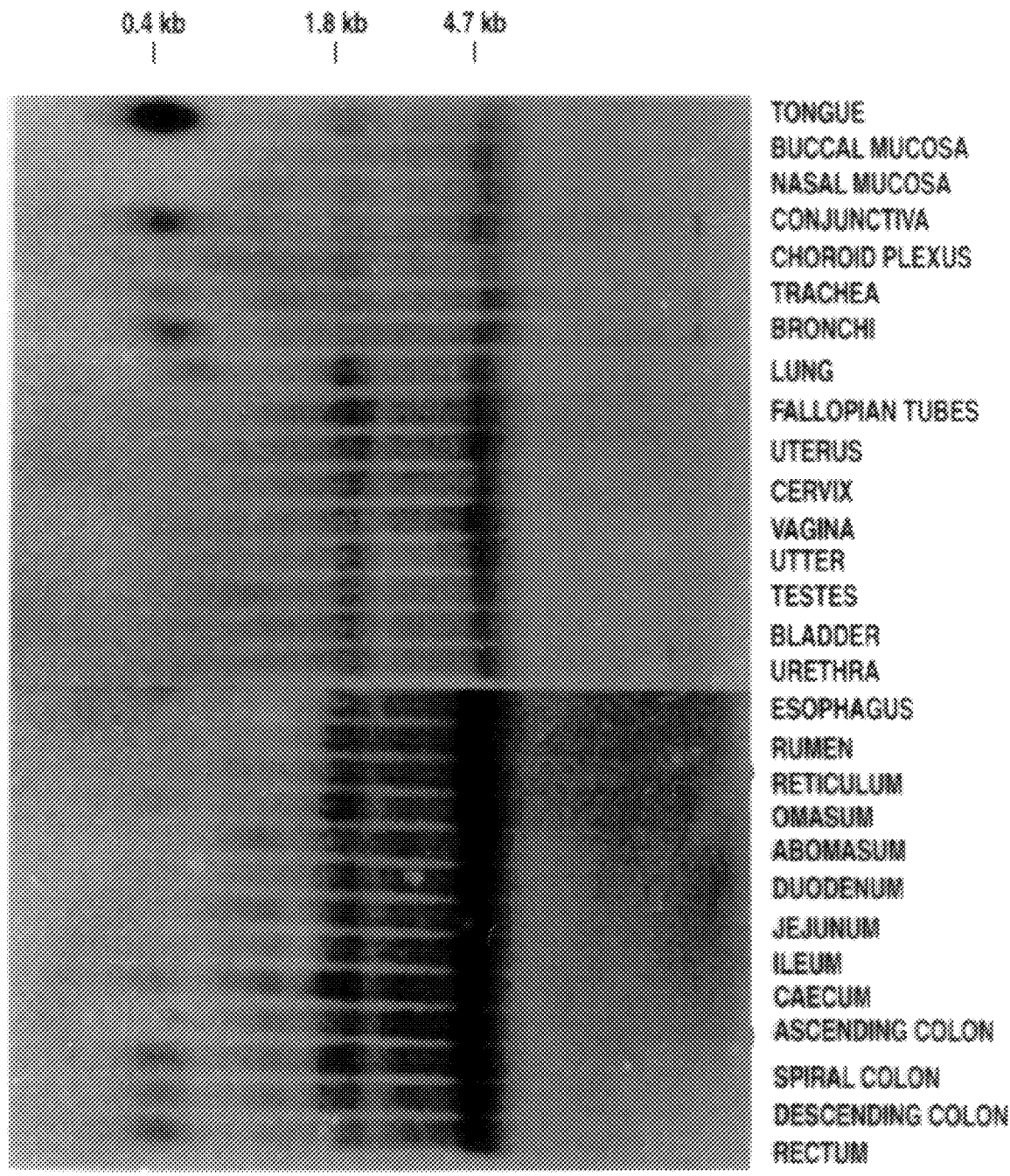

LAP mRNA (or closely homologous messages) were widely expressed in the numerous epithelial tissues of the bovine respiratory tract including trachea, bronchi, and bronchi/lung; lower gastrointestinal tract including cecum, colon, and rectum; reproductive system including testes; and facial epithelium including conjunctiva (FIG. 4). The finding that LAP or a closely related message is expressed in so many epithelial tissues suggests that LAP plays a role in epithelial defense in sites in addition to the tongue.

LAP message was not expressed in the fetal tongue but was expressed after birth (FIG. 4). This pattern of expression supports induction or developmental regulation. Thus, LAP mRNA appears to be expressed at a low constitutive level in normal bovine tongue after birth (FIG. 3A), and is induced to higher levels of expression in response to injury and infection. It is possible that LAP contributes to wound healing and/or playing a role in limiting the physical area of the infection and sterilize the tissue. Both mechanisms have been suggested previously for other defensins (Lehrer et al., Annual Rev. Immunol. 11: 105–128, 1993).

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention.

What is claimed is:

1. A method of identifying up-regulators of lingual antimicrobial peptide (LAP) comprising contacting an epithelial cell culture with a test substance and measuring the level of LAP mRNA to determine whether the test substance is an up-regulator.

2. A method of identifying up-regulators of lingual antimicrobial peptide (LAP) comprising the steps of:
    i. constructing an expression vector containing a LAP gene promoter operably linked to a reporter gene;
    ii. infecting a host cell with the expression vector;
    iii. culturing the host cell in the presence of test substances; and
    iv. measuring the level of mRNA or reporter gene expression to determine whether the test substance is an up-regulator.

3. The method of claim 2 wherein said reporter gene is chloramphenicol acetyl transferase or β-galactosidase.

* * * * *